United States Patent
Bowden et al.

(10) Patent No.: US 12,352,622 B2
(45) Date of Patent: Jul. 8, 2025

(54) SMARTPHONE-BASED OCT SYSTEMS AND METHODS

(71) Applicant: Vanderbilt University, Nashville, TN (US)

(72) Inventors: Audrey K. Bowden, Nashville, TN (US); Joseph D. Malone, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 161 days.

(21) Appl. No.: 18/194,582

(22) Filed: Mar. 31, 2023

(65) Prior Publication Data

US 2023/0314123 A1  Oct. 5, 2023

Related U.S. Application Data

(60) Provisional application No. 63/326,188, filed on Mar. 31, 2022.

(51) Int. Cl.
*G01J 3/02* (2006.01)
*A61B 5/00* (2006.01)
(Continued)

(52) U.S. Cl.
CPC .......... *G01J 3/0208* (2013.01); *A61B 5/0066* (2013.01); *G01B 9/02091* (2013.01); *G01J 3/2803* (2013.01); *G02B 5/0278* (2013.01); *G06T 5/80* (2024.01); *H04M 1/0202* (2013.01); *G06T 2207/10024* (2013.01); *G06T 2207/10101* (2013.01); *G06T 2207/30024* (2013.01)

(58) Field of Classification Search
None
See application file for complete search history.

(56) References Cited

U.S. PATENT DOCUMENTS

2015/0055137 A1* 2/2015 Brown ............... G01B 9/02054
356/479
2017/0293121 A1* 10/2017 Kawamura ........ G02B 27/0025
(Continued)

FOREIGN PATENT DOCUMENTS

AU  2012298253 A1 * 4/2014 ........... A61B 5/0066
CA  2887361 A1 * 4/2014 ........... A61B 5/0035
(Continued)

OTHER PUBLICATIONS

Khan B., Wildey C., Francis R., Tian F., Delgado M.R., Liu H., Macfarlane D., Alexandrakis G. Improving optical contact for functional near-infrared brain spectroscopy and imaging with brush optodes. Biomed. Opt. Express. 2012;3:878-898.
(Continued)

*Primary Examiner* — Ricky Chin
(74) *Attorney, Agent, or Firm* — Michael Best & Friedrich LLP

(57) ABSTRACT

A smartphone-integrated OCT system to leverage the built-in components of smartphones for detection and processing, and/or display of OCT data. The smartphone-integrated optical coherence tomography system includes an optical coherence tomography (OCT) system, a smartphone, and a spectrometer configuration of optical components coupled to the optical coherence tomography system and the smartphone.

9 Claims, 11 Drawing Sheets

(51) Int. Cl.
| | |
|---|---|
| G01B 9/02091 | (2022.01) |
| G01J 3/28 | (2006.01) |
| G02B 5/02 | (2006.01) |
| G06T 5/80 | (2024.01) |
| H04M 1/02 | (2006.01) |

(56) References Cited

U.S. PATENT DOCUMENTS

| | | | | |
|---|---|---|---|---|
| 2018/0027159 | A1* | 1/2018 | Dillon | A61B 5/0088 |
| | | | | 348/66 |
| 2022/0015629 | A1* | 1/2022 | Seibel | A61B 3/12 |
| 2022/0256088 | A1* | 8/2022 | Bloch | H04N 25/76 |
| 2022/0282954 | A1* | 9/2022 | Volkov | G02B 27/34 |
| 2022/0357584 | A1* | 11/2022 | Eggleston | G01S 17/89 |
| 2022/0365336 | A1* | 11/2022 | Samanta | G01S 17/89 |
| 2023/0024072 | A1* | 1/2023 | Ji | G02B 6/1225 |
| 2023/0314123 | A1* | 10/2023 | Bowden | G01J 3/12 |
| | | | | 348/77 |
| 2024/0032827 | A1* | 2/2024 | Durr | A61B 5/743 |
| 2024/0203101 | A1* | 6/2024 | Zhang | G06V 20/70 |

FOREIGN PATENT DOCUMENTS

| | | | | |
|---|---|---|---|---|
| CA | 3238125 A1 * | 12/2018 | | A61B 3/0025 |
| CA | 3092259 A1 * | 9/2019 | | A61B 5/0035 |
| CA | 3100265 A1 * | 10/2020 | | A61F 9/00827 |
| CA | 3165710 A1 * | 7/2021 | | A61B 3/0008 |
| CA | 3234191 A1 * | 5/2023 | | A61B 3/0025 |
| CN | 110742575 A * | 2/2020 | | A61B 3/0008 |
| CN | 211426245 U * | 9/2020 | | G01N 21/01 |
| CN | 112545449 A * | 3/2021 | | |
| DE | 102016121246 A1 * | 5/2018 | | A61B 3/0016 |
| EP | 3757648 A1 * | 12/2020 | | G02B 21/0008 |
| WO | WO-2010009450 A1 * | 1/2010 | | A61B 3/0025 |
| WO | WO-2014048573 A1 * | 4/2014 | | A61B 5/0059 |
| WO | WO-2015168157 A1 * | 11/2015 | | A61B 1/046 |
| WO | WO-2019222616 A1 * | 11/2019 | | A61B 3/102 |
| WO | WO-2023165081 A1 * | 9/2023 | | |

OTHER PUBLICATIONS

Kight, Emily, Iftak Hussain, and Audrey K. Bowden. "Low-cost, volume-controlled dipstick urinalysis for home-testing." JoVE (Journal of Visualized Experiments) 171 (2021): e61406.

Kim CK, Lee S, Koh D, Kim BM. Development of wireless NIRS system with dynamic removal of motion artifacts. Biomed Eng Lett. 2011;1(4):254-259.

Kim, Sanghoon, et al. "Design and implementation of a low-cost, portable OCT system." Biomedical optics express 9.3 (2018): 1232-1243.

Kumar, Anupam, et al. "User-centric hardware and software development for low-cost naturalistic neuroimaging using fNIRS." Optical Tomography and Spectroscopy. Optica Publishing Group, 2022, 2 pages.

Kurz E.M., Wood G., Kober S.E., Schippinger W., Pichler G., Müller-Putz G., Bauernfeind G. Towards using fNIRS recordings of mental arithmetic for the detection of residual cognitive activity in patients with disorders of consciousness (DOC) Brain Cogn. 2018;125:78-87.

Landowska A, Royle S, Eachus P, Roberts D. Testing the Potential of Combining Functional Near-Infrared Spectroscopy with Different Virtual Reality Displays-Oculus Rift and oCtAVE. In: Jung, T and Dieck M, ed. Augmented Reality and Virtual Reality: Empowering Human, Place and Business. Progress in IS. ; 2018:309-321.

Lange F., Dunne L., Hale L., Tachtsidis I. Maestros: a multiwavelength time-domain NIRS system to monitor changes in oxygenation and oxidation state of cytochrome-C-oxidase. IEEE J. Sel. Top. Quantum Electron. 2019;25.

Lee, Kyung Chul, et al. "A smartphone-based Fourier ptychographic microscope using the display screen for illumination." ACS Photonics 8.5 (2021): 1307-1315.

Liu Y., Ayaz H. Speech recognition via fNIRS based brain signals. Front. Neurosci. 2018;12.

Machado A, Cai Z, Pellegrino G, et al. Optimal positioning of optodes on the scalp for personalized functional near-infrared spectroscopy investigations. J Neurosci Methods. 2018;309(Nov. 2017):91-108.

Malone, Joseph D., et al. "DiffuserSpec: spectroscopy with Scotch tape." Optics Letters 48.2 (2023): 323-326.

McGreevey, S. Finding signs of life when it matters most. The Harvard Gazette. Jul. 20, 2017. Available online at https://news.harvard.edu/gazette/story/2017/07/using-fmri-eeg-to-search-for-consciousness-in-icu-patients/ (3 pages).

McKendrick R., Mehta R., Ayaz H., Scheldrup M., Parasuraman R. Prefrontal hemodynamics of physical activity and environmental complexity during cognitive work. Hum. Factors. 2017;59(1):147-162.

Mehta, Rajvi, et al. "Wireless, web-based interactive control of optical coherence tomography with mobile devices." Translational Vision Science & Technology 6.1 (2017): 5-5.

Meng, Xin, et al. "Smartphone based hand-held quantitative phase microscope using the transport of intensity equation method." Lab on a Chip 17.1 (2017): 104-109.

Merzagora A.C., Schultheis M.T., Onaral B., Izzetoglu M. Functional near-infrared spectroscopy-based assessment of attention impairments after traumatic brain injury. J. Innov. Opt. Health Sci. 2011;04(03):251-260.

Mihajlovic V, Grundlehner B, Vullers R, Penders J. Wearable, wireless EEG solutions in daily life applications: What are we missing? IEEE J Biomed Heal Informatics. 2015;19(1):6-21.

Mihajlovic V, Patki S, Xu J. Noninvasive Wearable Brain Sensing. In: IEEE Sensors Journal. vol 18. IEEE Sensors. ; 2017:1661-1663.

Morikawa, Chamin, et al. "Image and video processing on mobile devices: a survey." The Visual Computer 37.12 (2021): 2931-2949.

Moshiri, Yasman, et al. "Handheld swept-source optical coherence tomography with angiography in awake premature neonates." Quantitative Imaging in Medicine and Surgery 9.9 (2019): 1495.

Murphy K., Harris A.D., Wise R.G. Robustly measuring vascular reactivity differences with breath-hold: normalising stimulus-evoked and resting state BOLD fMRI data. Neuroimage. 2011;54:369-379.

Nakamura, Yoshifumi, et al. "High-speed three-dimensional human retinal imaging by line-field spectral domain optical coherence tomography." Optics express 15.12 (2007): 7103-7116.

NewmanBrain. fNIR BrainSpy 28, (n.d.). Version dated Jan. 24, 2022. Available online at https://web.archive.org/web/20220124232555/https://www.newmanbrain.com/fnir-brainspy-28/ (5 pages).

NPS Medicinewise. Antibiotics, explained. Version accessed on Mar. 23, 2022. Retrieved from https://web.archive.org/web/20220323102023/https://www.nps.org.au/consumers/antibiotics-explained (4 pages).

OBELAB. NIRSIT Operator's Manual, 2016 (45 pages).

OBELAB. Nirsit-Lite Kids Brain Imaging System for Kids. Brochure. 2020. Available online at http://obelab.com/upload_file/down/Nirsit-Lite(kids)Brochure-research(eng2020).pdf (2 pages).

Obrig H. NIRS in clinical neurology a 'promising' tool? Neuroimage. 2014;85:535-546.

Obrig, Hellmuth, et al. "Near-infrared spectroscopy: does it function in functional activation studies of the adult brain?." International Journal of Psychophysiology 35.2-3 (2000): 125-142.0.

Pfeifer M.D., Scholkmann F., Labruyère R. Signal processing in functional near-infrared spectroscopy (fNIRS): methodological differences lead to different statistical results. Front. Hum. Neurosci. 2018;11:1-12.

Pi, Shaohua, et al. "Imaging retinal structures at cellular-level resolution by visible-light optical coherence tomography." Optics letters 45.7 (2020): 2107-2110.

Pinti P, Aichelburg C, Gilbert S, et al. A Review on the Use of Wearable Functional Near-Infrared Spectroscopy in Naturalistic Environments. Jpn Psychol Res. 2018;60(4):347-373.

Pollonini L, Bortfeld H, Oghalai JS. Phoebe: a method for real time mapping of optodes-scalp coupling in functional near-infrared spectroscopy. Biomed Opt Express. 2016;7(12):5104.

(56) References Cited

OTHER PUBLICATIONS

Potter, L. Urinalysis—OSCE Guide. Version accessed Mar. 24, 2022, available online at https://web.archive.org/web/20220324195636/http://geekymedics.com/urinalysis-osce-guide/ (43 pages).

Quaresima V., Ferrari M. Functional Near-Infrared Spectroscopy (fNIRS) for assessing cerebral cortex function during human behavior in natural/social situations: a concise review. Organ. Res. Methods. 2019;22(1):46-68.

Rao, Adrit, and Harvey A. Fishman. "OCTAI: Smartphone-based Optical Coherence Tomography Image Analysis System." 2021 IEEE World AI IoT Congress (AIIoT). IEEE, 2021.

Romero-Ramirez, F.J. et al. Speeded up detection of squared fiducial markers, Image Vis. Comput. 76 (2018) 38-47.

Roy, Somak, et al. "Smartphone adapters for digital photomicrography." Journal of pathology informatics 5.1 (2014): 24.

Safaie J, Grebe R, Moghaddam HA, Wallois F. Toward a fully integrated wireless wearable EEG-NIRS bimodal acquisition system. J Neural Eng. 2013;10(5).

Saikia MJ, Besio WG, Mankodiya K. WearLight: Toward a Wearable, Configurable Functional NIR Spectroscopy System for Non-invasive Neuroimaging. IEEE Trans Biomed Circuits Syst. 2019;13(1):91-102.

Samsung. ISOCELL 2L4 Specifications. Version accessed on Nov. 2, 2021. Available oonline at https://web.archive.org/web/20211102045607/https://www.samsung.com/semiconductor/minisite/isocell/mobile-image-sensors/isocell-fast-2l4/ (8 pages).

Sappia, M.S. et al. Signal quality index: an algorithm for quantitative assessment of functional near infrared spectroscopy signal quality, Biomed. Opt. Express. 11 (2020) 6732.

Sato T. et al. Reduction of global interference of scalp-hemodynamics in functional near-infrared spectroscopy using short distance probes. Neuroimage. 2016;141:120-132.

Science of Psychotherapy. Prefontal Cortex webpage. Jan. 4, 2017. Version accessed Feb. 19, 2022. Available online at: https://www.thescienceofpsychotherapy.com/prefrontal-cortex/ (24 pages).

Shu, Xiao, et al. "Designing visible-light optical coherence tomography towards clinics." Quantitative Imaging in Medicine and Surgery 9.5 (2019): 769.

Si, Juanning, et al. "A portable fNIRS system with eight channels." Optical techniques in neurosurgery, neurophotonics, and optogenetics II. vol. 9305. SPIE, 2015.

Smith, G. T., et al. "Low-power, low-cost urinalysis system with integrated dipstick evaluation and microscopic analysis." Lab on a Chip 18.14 (2018): 2111-2123.

Smith, G. T., et al. "Robust dipstick urinalysis using a low-cost, micro-volume slipping manifold and mobile phone platform." Lab on a Chip 16.11 (2016): 2069-2078.

Smith, K. Urinalysis: How the Test Is Done and What Results Mean | Everyday Health. Version accessed Mar. 9, 2022, available online at https://web.archive.org/web/20220309073835/https://www.everydayhealth.com/urine/urinalysis-how-test-done-what-results-mean/ (14 pages).

Soetikno, Brian T., et al. "Inner retinal oxygen metabolism in the 50/10 oxygen-induced retinopathy model." Scientific reports 5.1 (2015): 1-14.

Song C, Jeon S, Lee S, Ha HG, Kim J, Hong J. Augmented reality-based electrode guidance system for reliable electroencephalography. Biomed Eng Online. 2018;17(1).

Song, Ge, et al. "First clinical application of low-cost OCT." Translational vision science & technology 8.3 (2019): 61-61.

Statista. "Smartphone subscriptions worldwide 2027 | Statista." Version accesssed Mar. 20, 2022. Available online at https://web.archive.org/web/20220320015240/https://www.statista.com/statistics/330695/number-of-smartphone-users-worldwide/ (2 pages).

Stillman A.E., Hu X., Jerosch-Herold M. Functional MRI of brain during breath holding at 4 T. Magn. Reson. Imaging. 1995;13(6):893-897.

Strangman G.E., Li Z., Zhang Q. Depth sensitivity and source-detector separations for near infrared spectroscopy based on the Colin27 brain template. PLoS One. 2013;8.

Sumner, Rob. "Processing raw images in matlab." Department of Electrical Engineering, University of California Sata Cruz 2 (2014).

Surre, Jérémy, et al. "Strong increase in the autofluorescence of cells signals struggle for survival." Scientific reports 8.1 (2018): 1-14.

Switz, Neil A., Michael V. D'Ambrosio, and Daniel A. Fletcher. "Low-cost mobile phone microscopy with a reversed mobile phone camera lens." PloS one 9.5 (2014): e95330.

Tamnes, Christian K., et al. "Development of the cerebral cortex across adolescence: a multisample study of inter-related longitudinal changes in cortical volume, surface area, and thickness." Journal of Neuroscience 37.12 (2017): 3402-3412.

Tankeshwar, A. Mueller Hinton Agar (MHA): Composition, preparation and uses. Jul. 20, 2013. Version accessed May 9, 2021, Retrieved from https://web.archive.org/web/20210509170120/https://microbeonline.com/why-mueller-hinton-agar-is-used-in-routine-antibiotic-susceptibility-testing/ (3 pages).

Teichman, Joshua C., Kashif Baig, and Iqbal Ike K. Ahmed. "Simple technique to measure toric intraocular lens alignment and stability using a smartphone." Journal of Cataract & Refractive Surgery 40.12 (2014): 1949-1952.

Teranaka, Hayato, et al. "Single-sensor RGB and NIR image acquisition: toward optimal performance by taking account of CFA pattern, demosaicking, and color correction." Electronic Imaging 2016.18 (2016): 1-6.

Thomason Moriah E., Burrows Brittany E., Gabrieli John D.E., Glover Gary H. Breath holding reveals differences in fMRI BOLD signal in children and adults. Neuroimage. 2005;25(3):824-837.

Tsow F., et al. Wearable Functional Near-Infrared (FNIR) Technology and Its Applications in Naturalistic Conditions, Am J Biomed Sci & Res. 2019-5(1). AJBSR.MS.ID.000869.

Tsow, Francis, et al. "A low-cost, wearable, do-it-yourself functional near-infrared spectroscopy (DIY-fNIRS) headband." HardwareX 10 (2021): e00204.

Uthoff, Ross D., et al. "Point-of-care, multispectral, smartphone-based dermascopes for dermal lesion screening and erythema monitoring." Journal of biomedical optics 25.6 (2020): 066004.

Von Lühmann A., Herff C., Heger D., Schultz T. Toward a wireless open source instrument: functional near-infrared spectroscopy in mobile neuroergonomics and BCI applications. Front. Hum. Neurosci. 2015;9:617.

Von Lühmann A., Wabnitz H., Sander T., Müller K. M3BA: a mobile, modular, multimodal biosignal acquisition architecture for miniaturized EEG-NIRS-based hybrid BCI and monitoring. IEEE Trans. Biomed. Eng. 2017;64:1199-1210.

Wang, Y. and Liu, X., 2021. Line field Fourier domain optical coherence tomography based on a spatial light modulator. Applied Optics, 60(4), pp. 985-992.

Wojtkowski, Maciej, et al. "Ultrahigh-resolution, high-speed, Fourier domain optical coherence tomography and methods for dispersion compensation." Optics express 12.11 (2004): 2404-2422.

World Health Organization. Causes of Antibiotic Resistance infographic. Version accessed Sep. 1, 2018. Available online at https://web.archive.org/web/20180901000034/https://www.phpnepal.org.np/images/PUBLICATION-NEWS/Global-Health/Causes-antibiotic-resistance.jpg (1 pages).

Wyser D., Lambercy O., Scholkmann F., Wolf M., Gassert R. Wearable and modular functional near-infrared spectroscopy instrument with multidistance measurements at four wavelengths. Neurophotonics. 2017;4.

Xing, Fangjian, et al. "Design and optimization of line-field optical coherence tomography at visible wavebands." Biomedical Optics Express 12.3 (2021): 1351-1365.

Yamada T., Umeyama S., Kamoshida A. Method for leveling the signal-to-noise ratio in multichannel functional near-infrared spectroscopy. Proc. SPIE. 2017.

Yaqub M. Atif, Woo Seong-Woo, Hong Keum-Shik. Compact, portable, high-density functional near-infrared spectroscopy system for brain imaging. IEEE Access. 2020;8:128224-128238.

Yi, Ji, et al. "Human retinal imaging using visible-light optical coherence tomography guided by scanning laser ophthalmoscopy." Biomedical optics express 6.10 (2015): 3701-3713.

Yücel MA, Lühmann A v., Scholkmann F, et al. Best practices for fNIRS publications. 2021;8(1):012101.

(56) References Cited

OTHER PUBLICATIONS

Zhang Q., Yan X., Strangman G.E. Development of motion resistant instrumentation for ambulatory near-infrared spectroscopy. J. Biomed. Opt. 2011;16:87008.

Zhang, Diming, and Qingjun Liu. "Biosensors and bioelectronics on smartphone for portable biochemical detection." Biosensors and Bioelectronics 75 (2016): 273-284.

Zhao Y., Qiu L., Sun Y., Huang C., Li T. Optimal hemoglobin extinction coefficient data set for near-infrared spectroscopy. Biomed. Opt. Express. 2017;8:5151-5159.

Zhao, H., & Cooper, R. J. (2018). Review of recent progress toward a fiberless, whole-scalp diffuse optical tomography system. Neurophotonics, 5(1), 011012-011012.

Zhou X, Sobczak G, Colette MM, Litovsky RY. Comparing fNIRS signal qualities between approaches with and without short channels. PLoS One. 2021;15(Dec. 12):1-18.

Almajidy R.K., Hofmann U.G. On the design of a multi-channel NIR system to monitor functional brain activity. NIR2013 Proc. 2013:335-338.

Arganda-Carreras, Ignacio, Carlos OS Sorzano, Roberto Marabini, José María Carazo, Carlos Ortiz-de-Solorzano, and Jan Kybic. "Consistent and elastic registration of histological sections using vector-spline regularization." In Computer Vision Approaches to Medical Image Analysis: Second International ECCV Workshop, CVAMIA 2006 Graz, Austria, May 12, 2006 Revised Papers 2, pp. 85-95. Springer Berlin Heidelberg, 2006.

Artemenko C., Soltanlou M., Ehlis A.C., Nuerk H.C., Dresler T. The neural correlates of mental arithmetic in adolescents: a longitudinal fNIRS study. Behav. Brain Funct. 2018;14:1-13.

Atsumori H., Kiguchi M., Katura T., Funane T., Obata A., Sato H., Manaka T., Iwamoto M., Maki A., Koizumi H., Kubota K. Noninvasive imaging of prefrontal activation during attention-demanding tasks performed while walking using a wearable optical topography system. J. Biomed. Opt. 2010;15.

Bale G., Elwell C.E., Tachtsidis I. From Jobsis to the present day: a review of clinical near-infrared spectroscopy measurements of cerebral cytochrome-c-oxidase. J. Biomed. Opt. 2016;21.

Beauchamp, M. S., et al. "The developmental trajectory of brain-scalp distance from birth through childhood: implications for functional neuroimaging." PloS one 6.9 (2011): e24981.

Bellina, Livia, and Eduardo Missoni. "Mobile cell-phones (M-phones) in telemicroscopy: increasing connectivity of isolated laboratories." Diagnostic pathology 4 (2009): 1-4.

Bhutta M.R., Hong K.S., Kim B.M., Hong M.J., Kim Y.H., Lee S.H. Note: three wavelengths near-infrared spectroscopy system for compensating the light absorbance by water. Rev. Sci. Instrum. 2014;85:2012-2015.

Blahnik, Vladan, and Oliver Schindelbeck. "Smartphone imaging technology and its applications." Advanced Optical Technologies 10.3 (2021): 145-232.

Breslauer, David N., et al. "Mobile phone based clinical microscopy for global health applications." PloS one 4.7 (2009): e6320.

Burggraaff, O., Schmidt, N., Zamorano, J., Pauly, K., Pascual, S., Tapia, C., Spyrakos, E. and Snik, F., 2019. Standardized spectral and radiometric calibration of consumer cameras. Optics express, 27(14), pp. 19075-19101.

Cavalcanti, Thiago C., et al. "Smartphone-based spectral imaging otoscope: System development and preliminary study for evaluation of its potential as a mobile diagnostic tool." Journal of Biophotonics 13.6 (2020): e2452.

Chenier F, Sawan M. A new brain imaging device based on fNIRS. Conf Proc—IEEE Biomed Circuits Syst Conf Healthc Technol BiOCAS2007. 2007;(December):1-4.

Chiarelli AM, Zappasodi F, di Pompeo F, et al. Flexible CW-fNIRS system based on Silicon Photomultipliers: In-Vivo characterization of sensorimotor response. In: 2017 IEEE Sensors. IEEE Sensors. ; 2017:1673-1675.

Chong, S.P., Bernucci, M., Radhakrishnan, H. and Srinivasan, V.J., 2017. Structural and functional human retinal imaging with a fiber-based visible light OCT ophthalmoscope. Biomedical optics express, 8(1), pp. 323-337.

Chong, Shau Poh, et al. "Ultrahigh resolution retinal imaging by visible light OCT with longitudinal achromatization." Biomedical optics express 9.4 (2018): 1477-1491.

Curtin A, Ayaz H. The Age of Neuroergonomics: Towards Ubiquitous and Continuous Measurement of Brain Function with fNIRS. Jpn Psychol Res. 2018;60(4, SI):374-386.

Dai, Bo, et al. "Colour compound lenses for a portable fluorescence microscope." Light: Science & Applications 8.1 (2019): 75.

Dempsey L.A., Cooper R.J., Roque T., Correia T., Magee E., Powell S., Gibson A.P., Hebden J.C. Data-driven approach to optimum wavelength selection for diffuse optical imaging. J. Biomed. Opt. 2015;20.

Dravida S, Ono Y, Noah JA, Zhang X, Hirsch J. Co-localization of theta-band activity and hemodynamic responses during face perception: simultaneous electroencephalography and functional near-infrared spectroscopy recordings. Neurophotonics. 2019;6(04):1.

Dsouza, Roshan, et al. "Economical and compact briefcase spectral-domain optical coherence tomography system for primary care and point-of-care applications." Journal of biomedical optics 23.9 (2018): 096003-096003.

Ellerbee, Audrey K., et al. "Quantifying colorimetric assays in paper-based microfluidic devices by measuring the transmission of light through paper." Analytical chemistry 81.20 (2009): 8447-8452.

Falk TH, Guirgis M, Power S, Chau TT. Taking NIRS-BCIs outside the lab: Towards achieving robustness against environment noise. IEEE Trans Neural Syst Rehabil Eng. 2011; 19(2):136-146.

Fechtig, Daniel J., et al. "Line-field parallel swept source interferometric imaging at up to 1 MHz." Optics Letters 39.18 (2014): 5333-5336.

Freeman, Esther E., et al. "Smartphone confocal microscopy for imaging cellular structures in human skin in vivo." Biomedical optics express 9.4 (2018): 1906-1915.

Funane, Tsukasa, et al. "Noncontact brain activity measurement system based on near-infrared spectroscopy." Applied Physics Letters 96.12 (2010): 123701.

Ga L., Yucel M., Boas D., Cooper R. Further improvement in reducing superficial contamination in NIRS using double short separation measurements. Bone. 2008;23:1-7.

Gagnon L., Perdue K., Greve D.N., Goldenholz D., Kaskhedikar G., Boas D.A. Improved recovery of the hemodynamic response in diffuse optical imaging using short optode separations and state-space modeling. Neuroimage. 2011;56 (3):1362-1371.

Gagnon Louis, Cooper Robert J., Yucel Meryem A., Perdue Katherine L., Greve Douglas N., Boas David A. Short separation channel location impacts the performance of short channel regression in NIRS. Neuroimage. 2012;59 (3):2518-2528.

Garrido-Jurado S, Muñoz-Salinas R, Madrid-Cuevas FJ, Medina-Carnicer R. Generation of fiducial marker dictionaries using Mixed Integer Linear Programming. Pattern Recognit. 2016;51(October):481-491.

Ge S, Yang Q, Wang R, et al. A Brain-Computer Interface Based on a Few-Channel IEEG-fNIRS Bimodal System. IEEE Access. 2017;5:208-218.

Glasser MF, Coalson TS, Robinson EC, et al. A multi-modal parcellation of human cerebral cortex. Nature. 2017;536 7615):171-178.

Hamilton, Antonia, et al. "Seeing into the brain of an actor with mocap and fNIRS." Proceedings of the 2018 ACM International Symposium on Wearable Computers. 2018.

Han, Le, et al. "Line-scanning SD-OCT for in-vivo, non-contact, volumetric, cellular resolution imaging of the human cornea and limbus." Biomedical Optics Express 13.7 (2022): 4007-4020.

He, Bin, et al. "Electrophysiological imaging of brain activity and connectivity-challenges and opportunities." IEEE transactions on biomedical engineering 58.7 (2011): 1918-1931.

He, Qinghua, and Ruikang Wang. "Hyperspectral imaging enabled by an unmodified smartphone for analyzing skin morphological features and monitoring hemodynamics." Biomedical optics express 11.2 (2020): 895-910.

(56) References Cited

OTHER PUBLICATIONS

Hirshfield, L.. "6.0 Development of a Remote-fNIRS Device." Version accessed Mar. 2, 2021, available online at https://web.archive.org/web/20210302150053/https://alivelearn.net/wp-content/uploads/2020/05/Leanne_remote_fnirs.pdf (17 pages).

Holtzer, Roee, et al. "fNIRS study of walking and walking while talking in young and old individuals." Journals of Gerontology Series A: Biomedical Sciences and Medical Sciences 66.8 (2011): 879-887.

Homan RW, Herman J, Purdy P. Cerebral location of international 10-20 system electrode placement. Electroencephalogr Clin Neurophysiol. 1987;66(4):376-382.

Huang, Xiwei, et al. "Smartphone-based analytical biosensors." Analyst 143.22 (2018): 5339-5351.

Hunt, B., Ruiz, A.J. and Pogue, B.W., 2021. Smartphone-based imaging systems for medical applications: a critical review. Journal of Biomedical Optics, 26(4), p. 040902.

Hussain, I. and Bowden, A.K., 2021. Smartphone-based optical spectroscopic platforms for biomedical applications: a review. Biomedical Optics Express, 12(4), pp. 1974-1998.

Idelson C.R., Vogt W.C., King-Casas B., LaConte S.M., Rylander C.G. Effect of mechanical optical clearing on near-infrared spectroscopy. Lasers Surg. Med. 2015;47:495-502.

Izzetoglu, K. et al. "Functional near-infrared neuroimaging," The 26th Annual International Conference of the IEEE Engineering in Medicine and Biology Society, San Francisco, CA, USA, 2004, pp. 5333-5336.

Jaffe-Dax S, Bermano AH, Erel Y, Emberson LL. Video-based motion-resilient reconstruction of three-dimensional position for functional near-infrared spectroscopy and electroencephalography head mounted probes. Neurophotonics. 2020;7(03):1.

Jasińska KK, Guei S. Neuroimaging field methods using functional near infrared spectroscopy (NIRS) neuroimaging to study global child development: Rural sub-Saharan Africa. J Vis Exp. 2018;2018(132):1-11.

Jurcak V, Tsuzuki D, Dan I. 10/20, 10/10, and 10/5 systems revisited: Their validity as relative head-surface-based positioning systems. Neuroimage. 2007;34(4):1600-1611.

Kassab A, Le Lan J, Tremblay J, et al. Multichannel wearable fNIRS-EEG system for long-term clinical monitoring. Hum Brain Mapp. 2018;39(1):7-23.

Kawaguchi H, Yamada T. A fNIRS probe positioning system using augmented reality technology. In: SPIE-Intl Soc Optical Eng; 2019:53.

Kazemi, V. et al. One millisecond face alignment with an ensemble of regression trees, Proc. IEEE Comput. Soc. Conf. Comput. Vis. Pattern Recognit. (2014) 1867-1874.

* cited by examiner

SMARTPHONE-BASED OCT SYSTEMS AND METHODS

CROSS-REFERENCE TO RELATED APPLICATIONS

This application is a non-provisional of and claims benefit of U.S. Provisional Patent Application No. 63/326,188, filed on Mar. 31, 2022, the entire contents of which are incorporated herein by reference.

STATEMENT REGARDING FEDERALLY SPONSORED RESEARCH OR DEVELOPMENT

This invention was made with government support under grant EY032670 awarded by the National Institutes of Health and grant W81XWH-20-1-0938 awarded by the Department of Defense. The government has certain rights in the invention.

BACKGROUND

In 2021, there were an estimated 6.2 billion smartphone users across the globe. The extreme popularity of smartphone devices has placed them at the center of technical innovation: modern smartphones are equipped with high-resolution camera systems, state-of-the-art computational and graphical processors, a wide array of electrical and mechanical sensors, powerful wireless communication capabilities and a variety of software development packages. Not surprisingly, smartphones feature widely in many contexts, including for clinical and scientific purposes, and several researchers have sought to integrate smartphone cameras into scientific imaging systems. For example, commercial microscopes outfitted with smartphone cameras circumvent the need for expensive scientific cameras. Some researchers have developed standalone devices, such as otoscopes, confocal and fluorescent microscopes and endoscopes, that leverage the portability and compact nature of the smartphone for low-resource applications. Still others have used the smartphone camera for multispectral or true spectroscopic imaging and analysis in advanced biosensing applications.

With the unprecedented technical innovation of smartphones in computational power and optical imaging capabilities, they are potentially invaluable tools in scientific imaging applications. The smartphone has a compact form-factor and broad accessibility that has motivated researchers to develop smartphone-integrated imaging systems for a wide array of applications. Optical coherence tomography (OCT) is one such technique that could benefit from the advantages of smartphone-integration.

Recent attempts to integrate smartphones into OCT data collection and processing pipelines have focused only on using the native computational and wireless connectivity capabilities of the smartphone to process or transmit data collected by a separate, more traditional OCT system. For example, one group demonstrated web-based interactive control of an OCT system, showing that remote access to OCT imaging that could enable advanced telemedicine evaluation of remote patient data. Another group used the smartphone as a mobile computational platform to perform deep learning-based image processing that can analyze and display key diagnostic features from standard clinical OCT images, showing that smartphone integration can reduce the need for bulky computers for processing. Neither of these demonstrations has shown integration of the smartphone camera for OCT data collection.

SUMMARY

As with the aforementioned scientific applications, OCT is a platform technology for bioimaging that could benefit from the capabilities provided by smartphones. A key benefit of smartphone integration is the ability to create more portable and affordable systems.

The present disclosure provides a smartphone-integrated OCT system to leverage the built-in components of smartphones for detection, processing, and display of OCT data. The example below demonstrates the use of a smartphone camera to capture interferometric OCT data at visible wavelengths, which overlap with the wavelength sensitivity of high-speed commercial smartphone sensors, and thus can be performed without tampering with the embedded color filters. Visible-wavelength OCT is a field of growing clinical significance that lacks low-cost and small form-factor options, of which smartOCT may be a promising implementation. Using a combination of custom and existing smartphone applications, real-time visualization of OCT B-scans and image processing directly on the smartphone was performed. This system design along with improvements to OCT technology could result in less expensive and more portable OCT devices at visible and near infrared wavelengths that can be used for clinical diagnostics in primary care suites, satellite clinics, and low-resource environments.

In some embodiments, the smartphone-integrated OCT system also can capture OCT data at non-visible wavelengths, which have a wavelength within the sensitivity range of the smartphone camera and filter. In some embodiments, the smartphone-integrated OCT system can use external components (e.g., upconverting nanoparticles and the like) to convert wavelengths outside the visible range into visible light that is detectable by the smartphone camera.

In some implementations, the systems and methods described herein present low-cost, portable (i.e., handheld) OCT systems that are integrated with a smartphone. In various implementations, the smartphone is used for detection, computation, display, and/or data transmission.

In one embodiment, the disclosure provides a smartphone-integrated optical coherence tomography system. The system includes an optical coherence tomography (OCT) system and a smartphone configured to receive a light signal from the OCT system. The light signal is generated by reflection from a sample, and the smartphone is configured to generate 2D OCT B-scans in real-time of the sample based on the light signal.

In another embodiment, the disclosure provides a smartphone-integrated optical coherence tomography system. The system includes an optical coherence tomography (OCT) system, a reverse-lens configuration optically coupled to the OCT system, and a smartphone configured to receive a light signal from the reverse-lens configuration. The light signal is generated by reflection from a tissue sample, and the smartphone is configured to generate 2D OCT B-scans in real-time of the tissue sample based on the light signal.

Other aspects of the invention will become apparent by consideration of the detailed description and accompanying drawings in the materials below.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Articles "a" and "an" are used herein to refer to one or to more than one (i.e., at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. As used herein, "and/or" refers to and encompasses any and all possible combinations of one or more of the associated listed items, as well as the lack of combinations where interpreted in the alternative ("or").

Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise indicated herein, and each separate value is incorporated into the specification as if it were individually recited herein. For example, if an intensity range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

Unless otherwise defined, all technical terms used herein have the same meaning as commonly understood by one of ordinary skill in the art to which this disclosure belongs.

OCT may be used in, for example, retinal imaging, brain imaging, interventional cardiology and gastroenterology for the detection and diagnosis of tumors, and in dermatology for the diagnosis of skin lesions.

Figure 1:
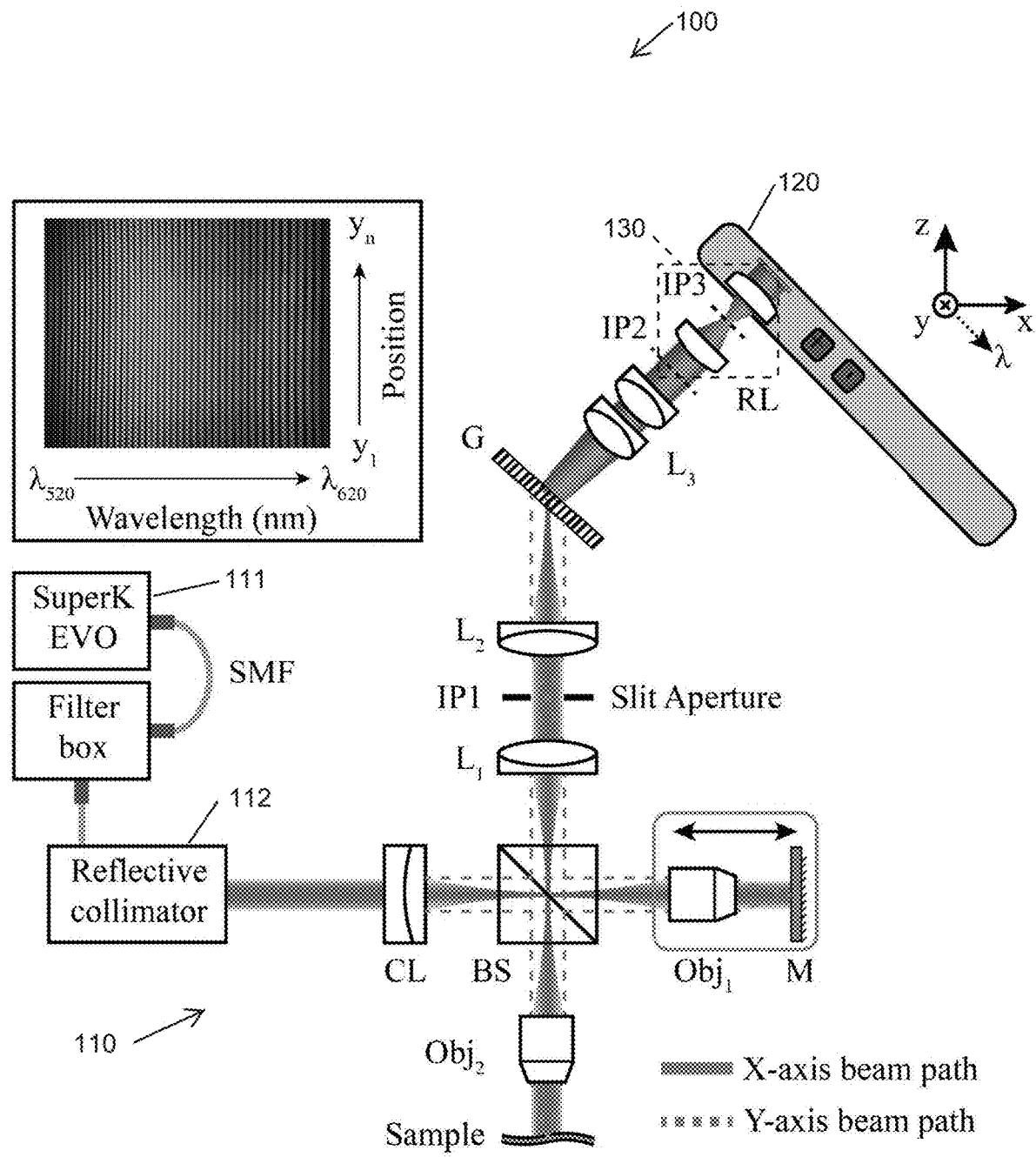
FIG. 1 is a schematic illustration of a smartphone-integrated OCT system according to an embodiment of the present disclosure.
Figure 12:
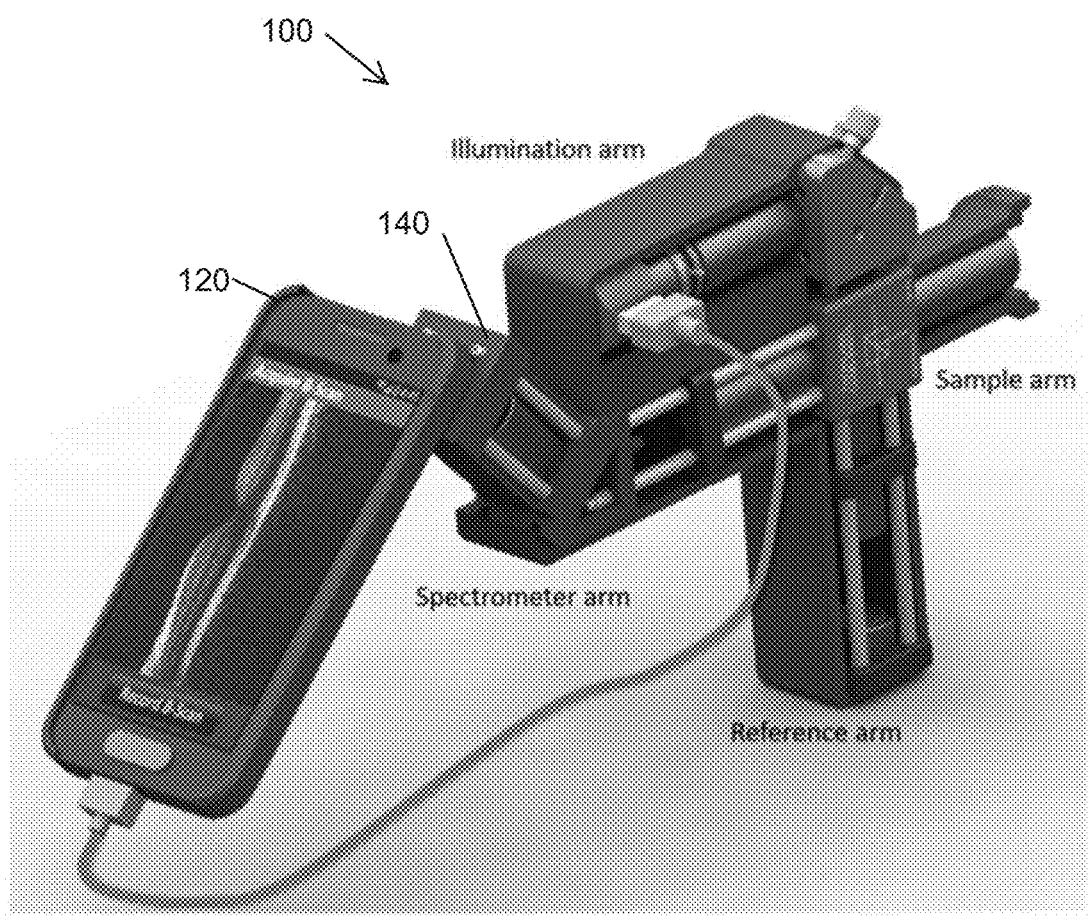
FIG. 12 is a perspective view of a smartphone-integrated OCT system according to an embodiment of the present disclosure.

FIGS. 1 and 12 schematically illustrate an example of a smartphone-integrated OCT system 100 for acquiring cross-sectional tomographic imaging of biological tissues or other objects with micrometer-scale spatial resolution. The system measures backscattered or backreflected light to generate images, which are two-dimensional data sets representing the optical backscattering in a cross-sectional plane through the biological tissue. FIG. 1 also illustrates a representative color interferogram showing the 2D spectrum from a mirror sample (top left inset) obtained with a line-field (LF-OCT) configuration. The blue box around the reference objective and mirror indicates that these components translate together.

In some implementations, the system 100 includes a LF-OCT configuration 110, a smartphone 120, a reverse-lens configuration 130 positioned between the LF-OCT configuration 10 and the smartphone 120, and a support platform 140 for the smartphone 120 as shown in FIG. 1. In other embodiments, the OCT configuration 110 can comprise other suitable OCT configurations, and the present disclosure is not limited to a specific LF-OCT configuration. The smartphone 120 includes a sensor (e.g., a camera), and the OCT configuration 110 uses the full two-dimensional (2D) smartphone sensor to capture 2D cross-sectional images of the tissue in a single frame. The use of a line-field OCT configuration (illustrated in FIG. 1 as one example) removes the need for mechanical scanners and allows single-shot B-scan imaging.

In some embodiments, the OCT configuration 110 includes a light source 111 and various optical components. In one embodiment, the light source is an LED light. In another embodiment, the light source 111 is a laser (e.g., an EUL-10, available from NKT Photonics) filtered to yield visible light. The laser beam output is first collimated using a reflective collimator 112 (e.g., RC04APC-P01, available from Thorlabs) and focused along the y-axis using a cylindrical lens CL (e.g., a 50-mm cylindrical lens 68-161, available from Edmund). The beam is then split into a sample arm and a reference arm using a beamsplitter BS (e.g., CCM5-BS016, available from Thorlabs) and focused along the x-axis of the sample and reference mirror, respectively, using objective lenses, $Obj_1$ and $Obj_2$ (e.g., 45-mm 4× objective lenses RMS4X, available from Thorlabs). The use of objective lenses can reduce the chromatic aberration in the system considering the broad bandwidth.

The returned light reflected off the sample is sent through a unit-magnification relay using two lenses $L_1$ and $L_2$ (e.g., 50-mm lenses AC254-050-A, available from Thorlabs) with a slit aperture (e.g., 50-μm) placed in the intermediate image plane IP1, conjugate to the sample and reference image planes. The slit aperture is used primarily to block extraneous reflections from lens surfaces and stray light.

The relayed light is spectrally dispersed using a dispersive element, such as a grating G (e.g., a 900-lpmm transmissive diffraction grating, available from Wasatch Photonics) with the focused line oriented orthogonal to the holographic features of the dispersive element. The dispersed beam is focused using a lens group $L_3$ (e.g., 25-mm focal length) at intermediate image plane 2, IP2. The 2D spectrum formed at IP2 was relayed to the smartphone sensor using a relay (e.g., 4-f unit-magnification) consisting of a plurality of smartphone lenses, symmetric about intermediate image plane 3, IP3. A reverse-lens RL is positioned on one side of the image plane IP3 while the smartphone lens is positioned on the opposite side of the image plane IP3. The RL can reduce distortion and minimize aberrations while imaging through native smartphone lenses.

The smartphone 120 is positioned on the support platform 130 relative to the reverse-lens RL to aid in alignment of the system 100. The support platform 130 can be 3D printed to conform to the smartphone 120.

Figure 2:
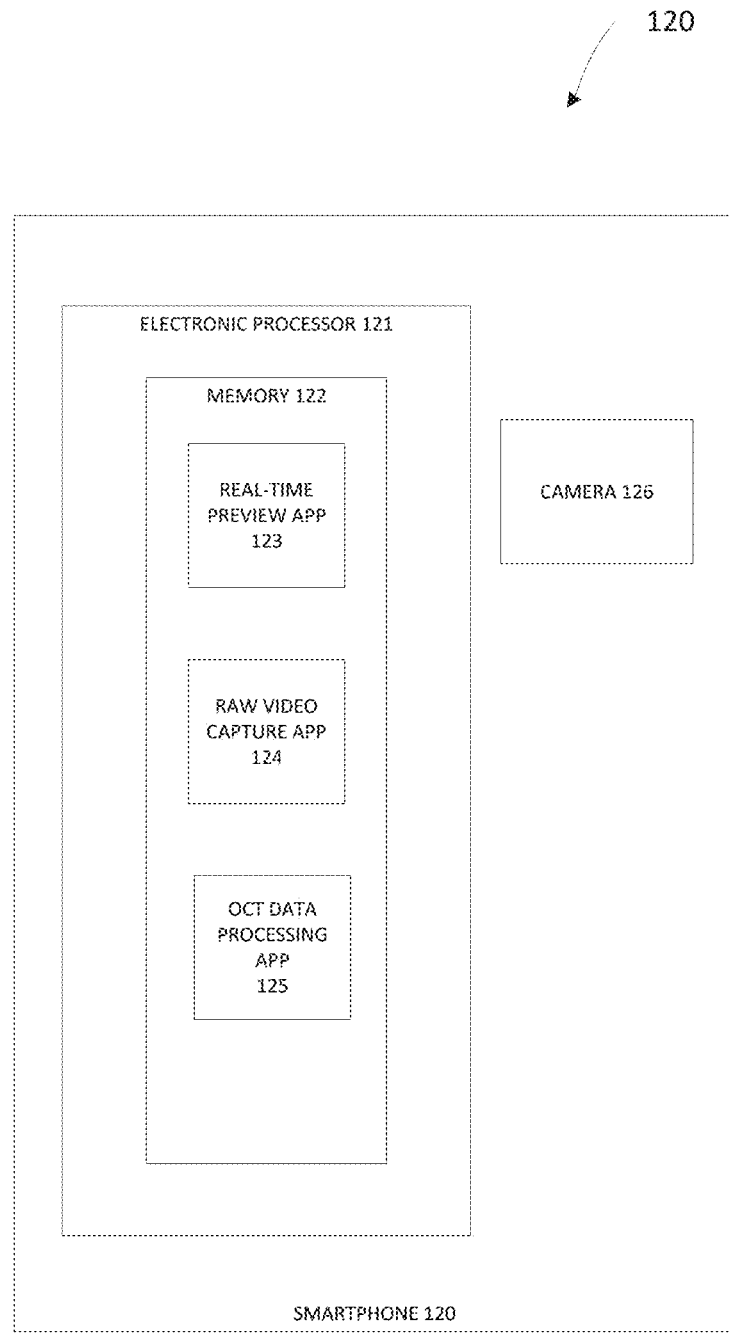
FIG. 2 is a schematic illustration of a smartphone used with the system illustrated in FIG. 1.

In some implementations, the smartphone 120 includes an electronic processor 121 and a non-transitory, computer-readable memory 122 as illustrated in FIG. 2. The memory 122 is communicatively coupled to the electronic processor 121 and stores instructions that are executed by the electronic processor 121 to provide output to a user interface, such as a display or screen on the smartphone 120. In some implementations, the memory 122 is also configured to store data including, for example, patient information and system configuration/calibration information. The smartphone 120 also includes a sensor or camera 126. The smartphone 120 includes other components and systems that are known in the art but are not described herein. The OCT data acquired by the smartphone 120 is processed for real-time viewing of OCT images of the sample.

With continued reference to FIG. 2, the memory 122 stores instructions in a real-time preview app 123, a RAW video capture app 124, and OCT data processing app 125.

Figure 3:
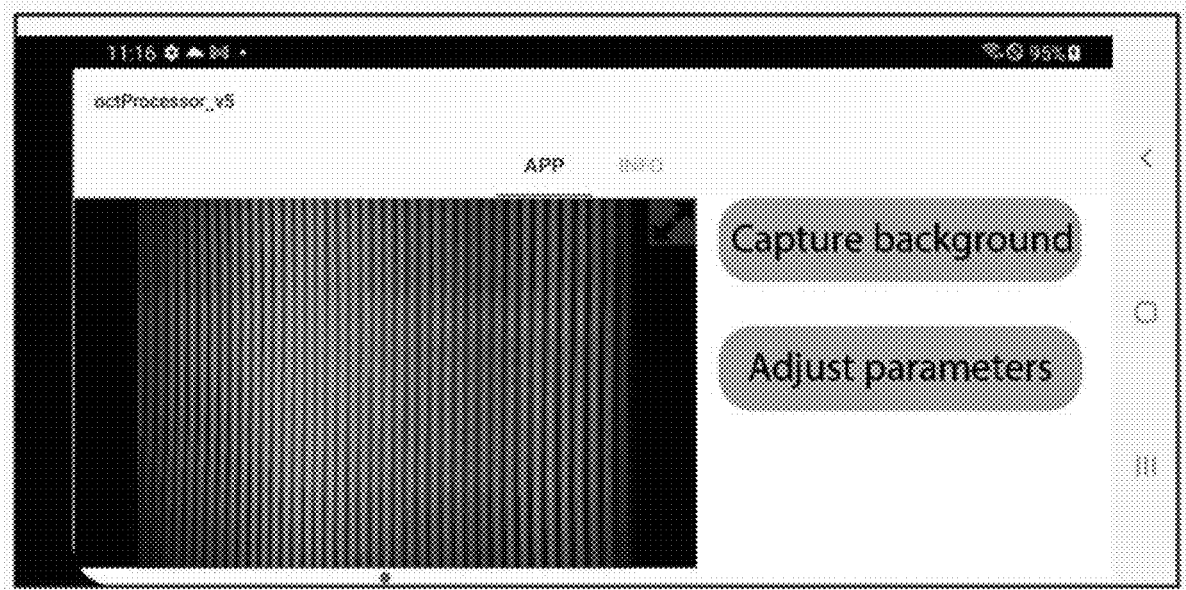
FIG. 3 is a screenshot of a real-time preview app stored and operated on the smartphone of FIG. 2 according to an embodiment of the present disclosure.
Figure 4:
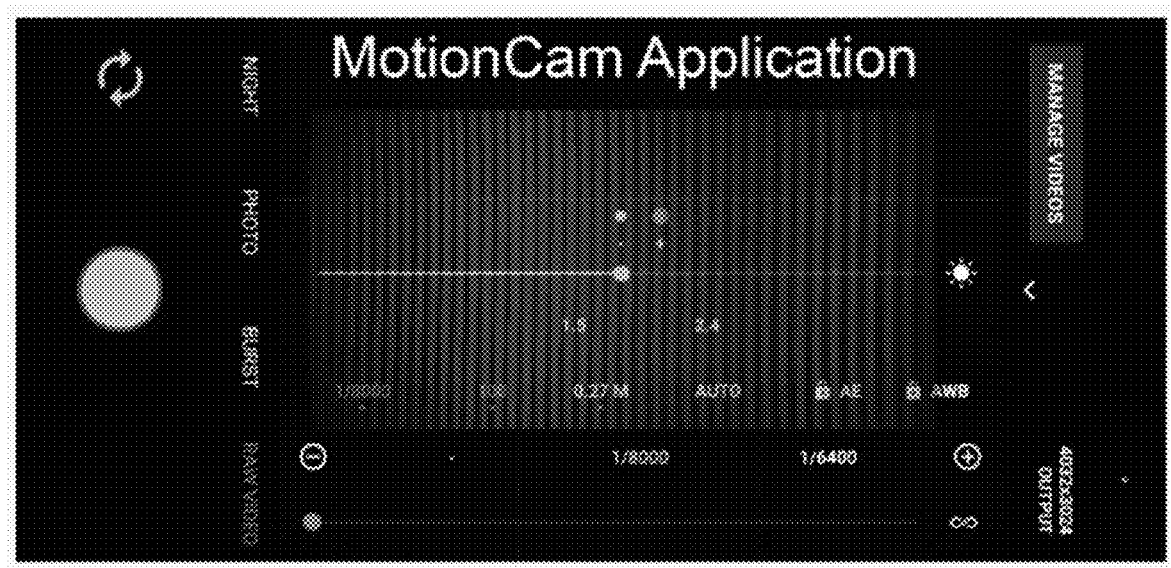
FIG. 4 is a screenshot of a RAW video capture app stored and operated on the smartphone of FIG. 2 according to an embodiment of the present disclosure.
Figure 5:
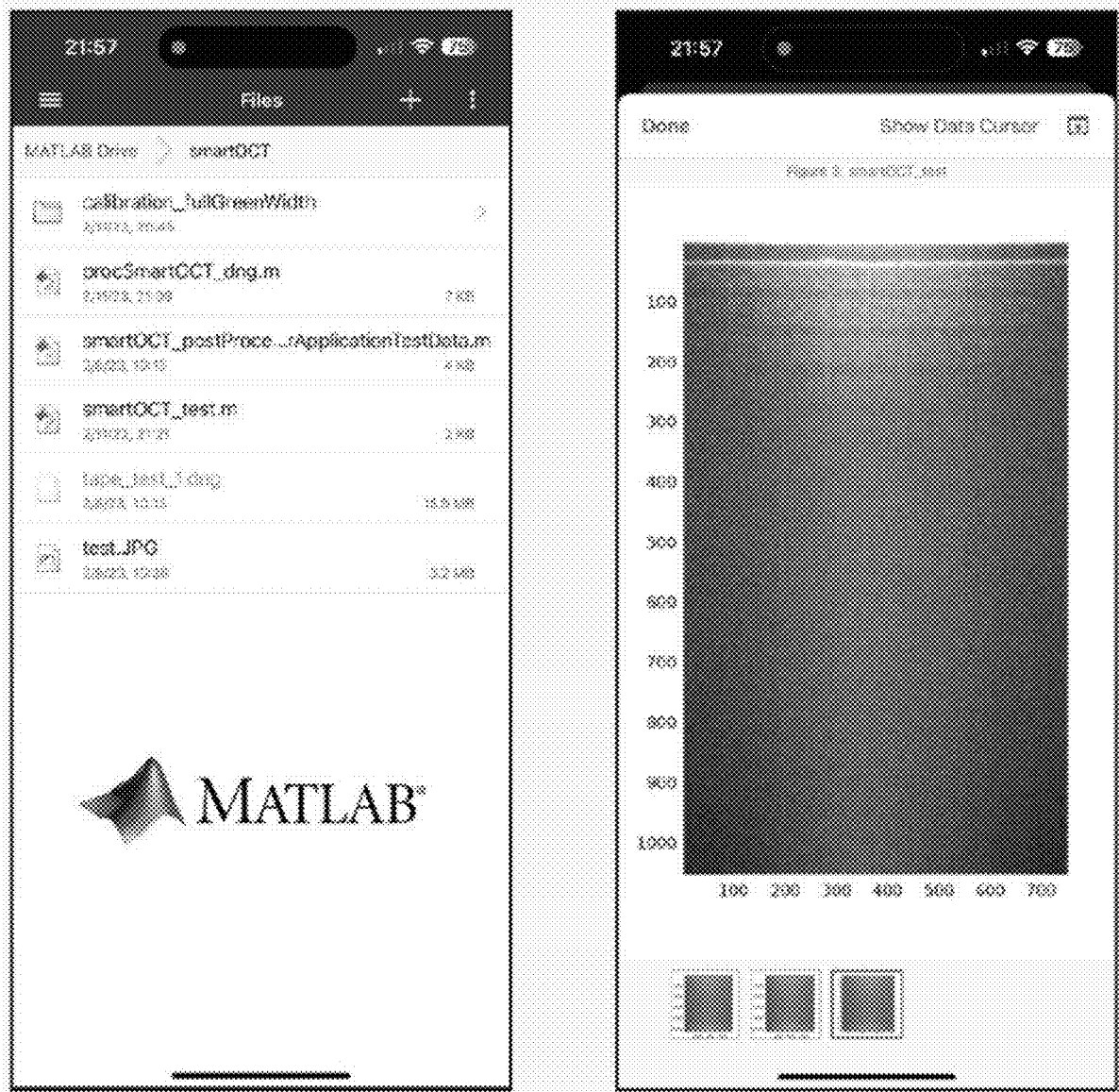
FIG. 5 is a screenshot of an OCT data processing app stored and operated on the smartphone of FIG. 2 according to an embodiment of the present disclosure.

The real-time preview app 123 provides live visualization of the OCT spectrum and processed B-scans for optimization and alignment of sample images. An example of output provided to the user interface on the smartphone 120 is illustrated in FIG. 3. The RAW video capture app 124 leverages an app (e.g., MotionCam), for RAW video capture. An example of output provided to the user interface on the smartphone 120 is illustrated in FIG. 4. The OCT data processing app 125 provides a processing pipeline to load and process OCT data directly on the smartphone 120 using a commercial app from MathWorks. An example of output provided to the user interface on the smartphone 120 is illustrated in FIG. 5.

The real-time preview app 123 functions to grab live image data from the smartphone camera system, performs basic OCT processing, and displays a 2D B-scan to the user. In one implementation, the real-time preview app 123 is a custom app developed with MATLAB Simulink and Android Studio. On opening the app, a user can choose to view the direct sensor output (2D spectra) or a processed B-scan by swiping left or right on the image. During app use, the sensor data (OCT spectra) are continuously read into the app back-end as three 8-bit RGB mp4 frames, merged into a full-color image (size 2280×1080 pixels) using the smartphone's internal visualization process within Simulink and displayed as a full-color image. In the real-time preview app 123, mp4 data or RAW data may be used for sample alignment and focus adjustment.

When visualizing OCT data, the user has the option to first capture a background image that will be used for background subtraction. If no image is selected, no subtraction is performed. When the app is switched to B-scan view, the app performs an OCT processing algorithm that begins by subtracting the background image and separating the green channel data from the red and blue channels. The red and blue channels are then omitted from further processing to reduce computational load. It was discovered that omitting these color channels had minimal effect on the preview quality, since the red and blue spectra were heavily attenuated in the selected wavelength range due to the Bayer filter. The green channel data were then resampled to be linear with respect to wavenumber using a calibrated polynomial function (the polynomial parameters can be adjusted within the app if a new calibration is performed). Finally, the fast-Fourier transform is performed, and the log of the 2D B-scan is displayed on the main user interface of the smartphone 120.

The RAW video capture app 124 uses, in one embodiment, the MotionCam for acquisition of 10-bit RAW videos of the 2D interferogram. While RAW data photography is a capability of the native S10 camera app, the camera app does not support RAW video capture. The MotionCam app enables simple tuning of camera settings such as exposure time, ISO and field-of-view (FOV) cropping. Data acquisition can be initiated by physical touch of the record button or by voice command. Once captured, the recorded data are saved to the smartphone 120 and/or external memory directly for processing. Switching between the apps is done by navigating to a shortcut menu on the smartphone homepage.

Figure 6:
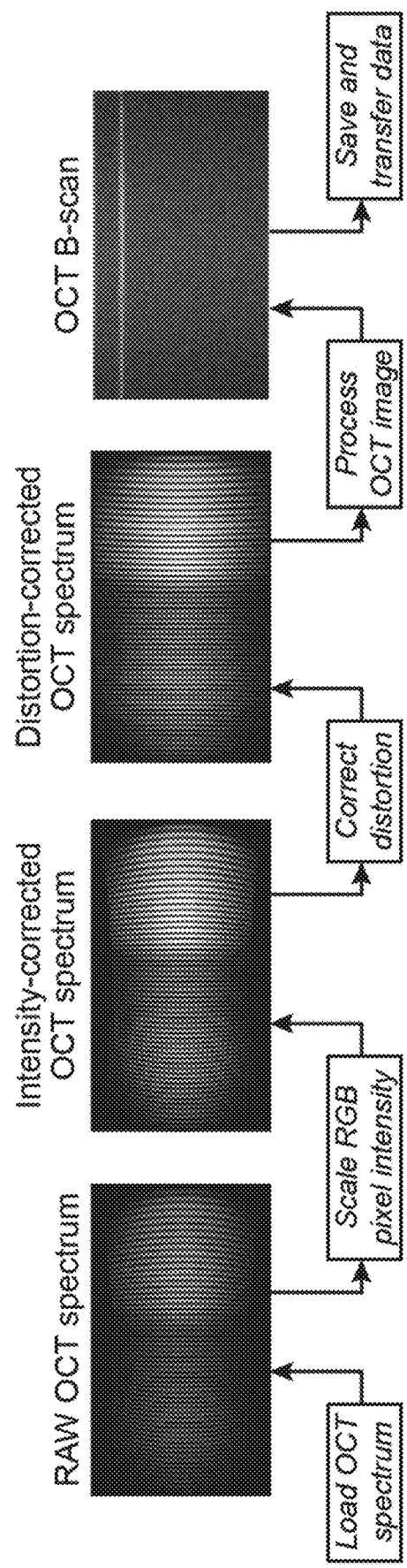
FIG. 6 is a flow diagram for RAW data processing by the OCT data processing app on the smartphone of FIG. 2 according to an embodiment of the present disclosure.

The OCT data processing app 125 is programmed to process the acquired RAW OCT interferograms. This app 125 uses, in one embodiment, the MatLab Mobile app, which enables the use of MatLab code loaded directly on the smartphone hardware. The processing pipeline is shown in FIG. 6, and it differs from the real-time preview app pipeline in that there are additional steps taken for intensity correction and distortion correction prior to OCT processing.

First, the RAW OCT spectrum is loaded into the processing app 125. On startup of the app 125, the processing script prompts the user to select the RAW dataset of interest from a folder in the smartphone's local memory 122. The data are loaded into the app as a 4032×1908×N-pixel (spectrum× position×frame) RGB-mosaicked image stack. The image size is automatically cropped relative to the full sensor size (4032×3024) when loaded to remove the inactive pixels specified in the RAW meta-information.

Figure 7:
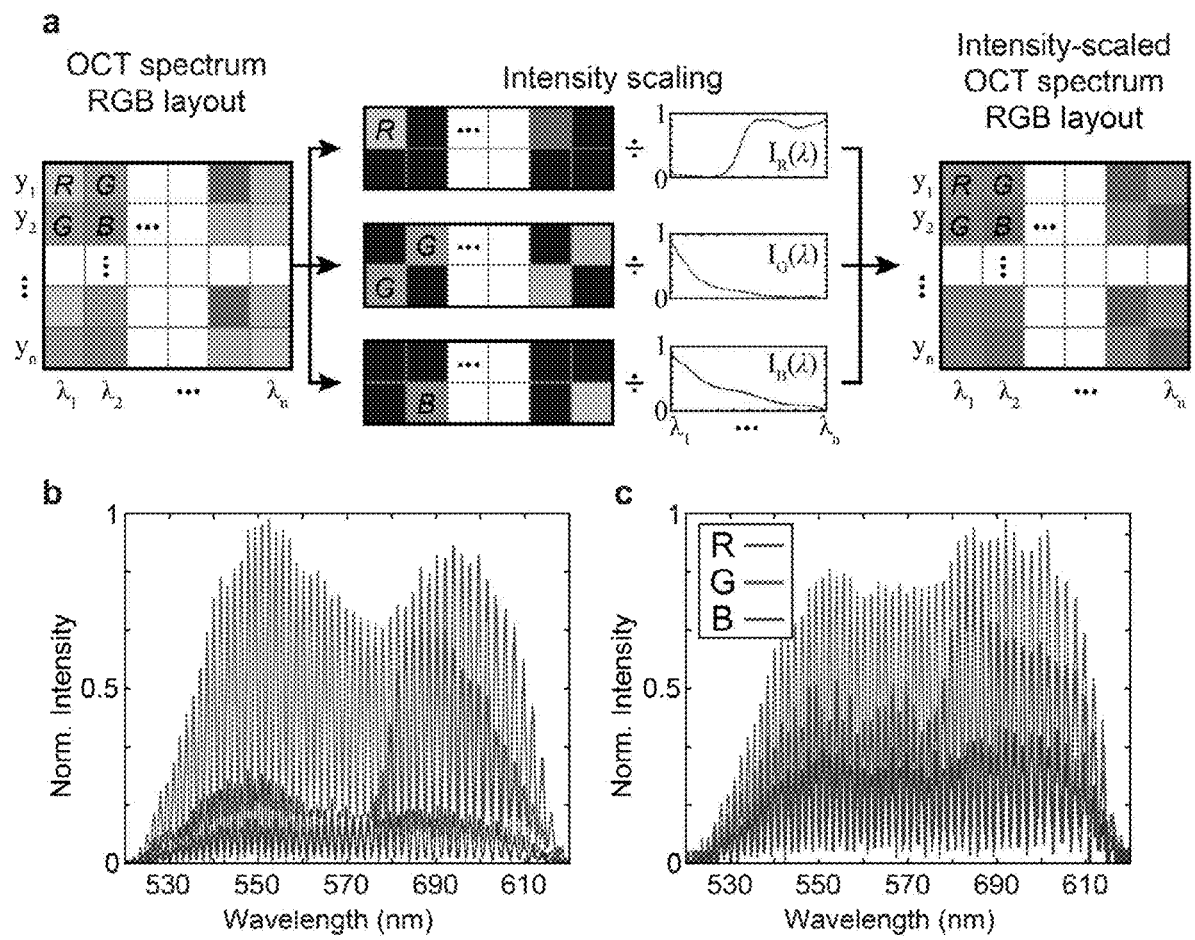
FIG. 7 illustrates an intensity scaling of RGB pixels. (a) The value of each RGB pixel of the RAW OCT spectrum is scaled by dividing it by the corresponding attenuation function. (b) Representative OCT interferogram taken from the center of the FOV of a mirror sample before and (c) after intensity scaling.

Second, RGB pixel values are scaled to compensate for the Bayer filter attenuation, yielding an intensity-corrected OCT spectrum. The intensity of each RGB pixel is then scaled to compensate for the non-uniform spectral attenuation of the Bayer filter. This intensity correction is accomplished by dividing each R, G, and B pixel of the RAW OCT spectrum with an intensity value derived from a color-specific, normalized, spectral attenuation function (FIG. 7 (at a)). The result of this operation is a spectral reshaping that compensates for the spectral attenuation induced by the Bayer filter. FIG. 7 (at b and c) show three 1D RGB plots of a representative interferogram taken from the center of the FOV of a mirror sample before and after intensity correction.

Third, the spectrum is sent through a distortion-correction algorithm. The intensity-corrected data are sent through a custom distortion-correction algorithm, described below, that compensates for the distortions caused by the system imaging optics, including the additional optics associated with the OCT engine. In brief, a B-spline unwarping transform is used to apply the correction.

Finally, the corrected spectral data are run through OCT processing pipeline consisting of background subtraction, k-space linearization, dispersion compensation, Fourier transformation and log compression before being stored. The corrected spectral image is then processed using traditional OCT methods. Background subtraction is performed, followed by resampling of the spectral data to be linear with respect to wavenumber using a polynomial function obtained via pixel-to-wavelength calibration of the spectrometer (discussed below). Next, the resampled spectrum is multiplied by a Hanning window, and system dispersion is corrected. Finally, the fast Fourier transform is performed and the log of the transformed data are displayed on the user interface of the smartphone 120. The processed data can then be stored locally using the smartphone internal memory 122 or on a local machine through wired USB-C connection. Using the MatLab app or the smartphone's native file system, the user can transfer data wirelessly to any local or remote device.

Extracting the distortion-correction coefficients need only be performed once for a given imaging configuration. The distortion correction method involves imaging a grid chart of known spacing in the sample plane and using a B-spline unwarping transform to align the measured grid with a synthesized ground truth image of the same grid. The grid target (e.g., R1L3S3P, available from Thorlabs) had a 500-μm spacing at the focus of the sample arm. Because system was designed for line imaging, a single point on the illumination line that was incident on a grid line resulted in linear spectrum. To increase the contrast between the spectrum and grid lines, the grid target was placed slightly out of focus, which resulted in dark lines on the spectrum, as shown in FIG. 8 (at a and b).

The resulting 2D spectrum is processed by first segmenting and binarizing the individual grid lines. Then, ten lateral positions on each binarized line, spaced 100 pixels apart, are selected as "source" point coordinates, which resulted in 70 source points (white circles, FIG. 8 (at c)). Target "ground-truth" points (red circles, FIG. 8 (at c)) are identified by first selecting the centermost source coordinate (at the center of the field-of-view) and calculating the X- and y-axis pixel offset to the next closest source point. These offsets are used as the target point spacings to form a uniform grid with the same number of target points as source points. This method only accounts for distortions along the y-axis (i.e., lateral position distortions) since spectral distortions are compensated during k-space linearization. Following point identification, the source points are registered to the target points using a non-linear unwarping transform (e.g., bUnwarpJ, available from FIJI). Next, the raw transform coefficients are saved to the calibration file and used as inputs in the main processing code to unwarp each 2D spectral frame prior to OCT processing.

Figure 8:
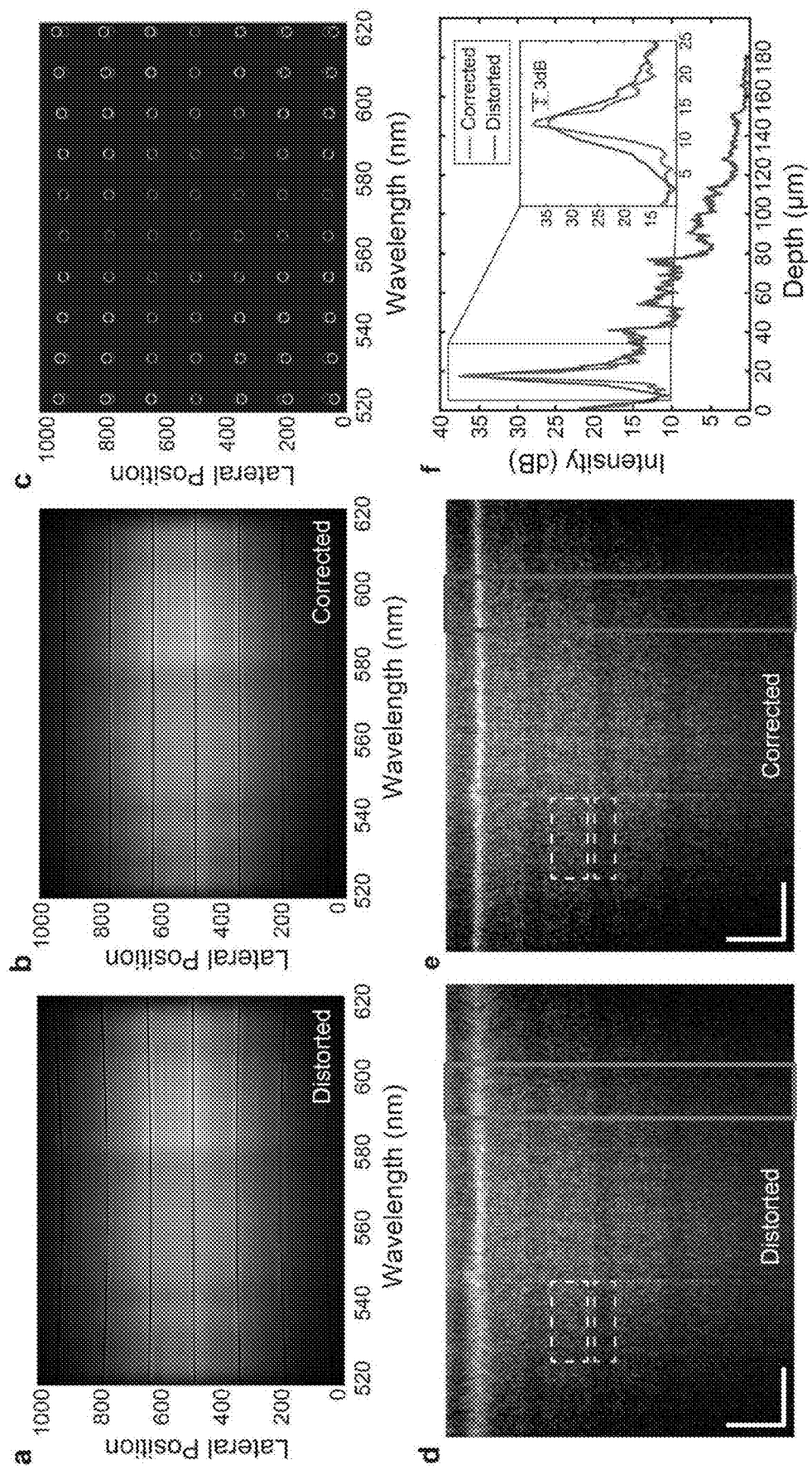
FIG. 8 illustrates distortion correction of a smartOCT spectrum. (a) Unprocessed, distorted RGB spectrum of a grid chart with 0.5-mm spacing captured on the smartphone. (b) Distortion-corrected spectrum. (c) Source (white) and target (red) points used for establishing the unwarping transform. (d) Original distorted OCT B-scan of Scotch tape and (e) distortion-corrected OCT B-scan. The white and yellow dotted boxes correspond to the regions used as signal and background in the SCR calculation, respectively. The blue and magenta boxes represent the regions that were averaged and plotted in panel (f), which shows an averaged A-scan. Scale bars are 250 µm along the positional axis (horizontal) and 50 µm along the depth axis (vertical).

FIG. 8 (at d and e) show a representative B-scan image of Scotch tape before and after the correction. The surface of the tape looks similar in the central portion of the field of view where there are minimal distortions. Toward the outer edges of the field of view (left and right of center), the surface of the tape in FIG. 8 (at d) is significantly blurred when compared to the same region in the corrected image. To illustrate this point, the data within the blue and magenta boxes of the distorted and corrected B-scans, respectively, are averaged along the lateral (position) axis to enhance contrast and plotted in FIG. 8 (at f). The plots show a sharpened surface peak around the 20 μm depth position with a 3 dB SNR improvement (boxed inset in FIG. 8 (at f)) and overall improved contrast between tape layers. Quantitatively, a speckle contrast ratio (SCR) was calculated between the second tape layer and tape gap for both images (shown as white and yellow boxes, respectively, in FIG. 8 (at d and e)), which resulted in a SCR of 1.52 and 1.66 for distorted and corrected B-scans, respectively.

Spectrometer calibration was performed by leveraging the wavelength tunability of the supercontinuum laser source and filter unit. Using the NKT control software, the wavelength output of the source was set to a 10-nm bandwidth (the minimum bandwidth of this unit) centered at 520 nm. The source was then swept across each 10-nm sub-band in steps of 10 nm, and a RAW video (frames are averaged in processing to reduce noise) of the 2D spectrum was captured at each of 11 sequential wavelength values from 520-620 nm. To extract the pixel associated with each wavelength, each 2D sub-band spectrum was corrected for distortion and then fit to a Gaussian profile along the spectral axis. The pixel value corresponding to the peak location of the fit was identified and estimated as the center wavelength of that sub-band. Since the output of each filtered sub-band was inherently Gaussian, this method produced a reliable and repeatable calibration. A third-order polynomial fit was then calculated to provide a pixel-to-wavelength mapping function for each row of the OCT spectral data. Notably, the mapping was not the same for each row, which relates to distortion along the spectral axis.

Example—Comparison of MP4 and Raw Data Acquired by the Smartphone-Integrated OCT System One consideration when integrating a smartphone with OCT hardware was the coupling of the smartphone camera unit to the spectrometer optics in its native condition without tampering (i.e., removing components such as the lens or sensor filters or additional modification of the smartphone). It would be helpful for future deployment in real-world environments if the smartphone did not require modification for use with OCT hardware. The main hardware considerations for smartphone selection were the number of sensor pixels, pixel size and exposure time, which impact the imaging depth, spectral sampling density and susceptibility to motion and fringe washout, respectively.

The Samsung Galaxy S10 smartphone was selected in this example largely because of its processing capabilities, capacity for low exposure time and availability of versatile data formats. The Sony ISOCELL 2L4 sensor features a 4032×3024 (width×height) RGB color pixel layout with a pixel size of 1.4 µm. The S10 camera unit enabled image acquisition at 30 fps at full resolution with a tunable exposure time from 33.3 ms-40 µs (30 Hz-24 kHz) per frame. In software, the native camera app enables "pro" picture and video modes that provide access to tuning of camera features (i.e., ISO, exposure time, frame size, etc.). Notably, the usability of various features through the native camera app during video-mode acquisition was somewhat limited, and the user could only tailor certain sensor settings under predetermined modes.

Many commercial smartphone camera systems prioritize simplicity (for the user) over custom setting controls. This made it difficult to control camera settings and access direct unprocessed sensor data, as one would typically when using a scientific camera. Moreover, photos and recorded videos captured with smartphones are subject to several proprietary internal processing steps, such as color-space linearization and dynamic non-linear color tuning, which are intended to make photographic pictures look better and are not representative of the true color and/or intensity of the incident light. Moreover, images acquired through native software are compressed when saved, which can further impact the fidelity of scientific images. Fortunately, smartphones are now a major technical platform for professional media creation, which has motivated the accessibility of unprocessed image data for custom image processing. The S10 enables RAW data capture for pictures, and community-designed open-source apps have made it possible to capture RAW video data, which was leveraged in this example. RAW data is understood to be any image file that contains an uncompressed image of direct sensor counts per pixel together with meta-information about the image collected from the sensor. Often the meta-information files contain information about the sensor model, color space specifications, preset calibration values (such as white balance multipliers), active area image width and height, etc. While many proprietary commercial variations of RAW data files are used, the common file format Digital Negative (DNG) has become a standard in the industry, and several software packages are available to convert proprietary file types into DNG formats. The RAW sensor data from the S10 was output as a DNG image type. For the remainder of this discussion, the capitalized term 'RAW' is used when referring to the DNG file type. Below is a discussion on the importance for RAW data processing and its impact on OCT data.

Figure 9:
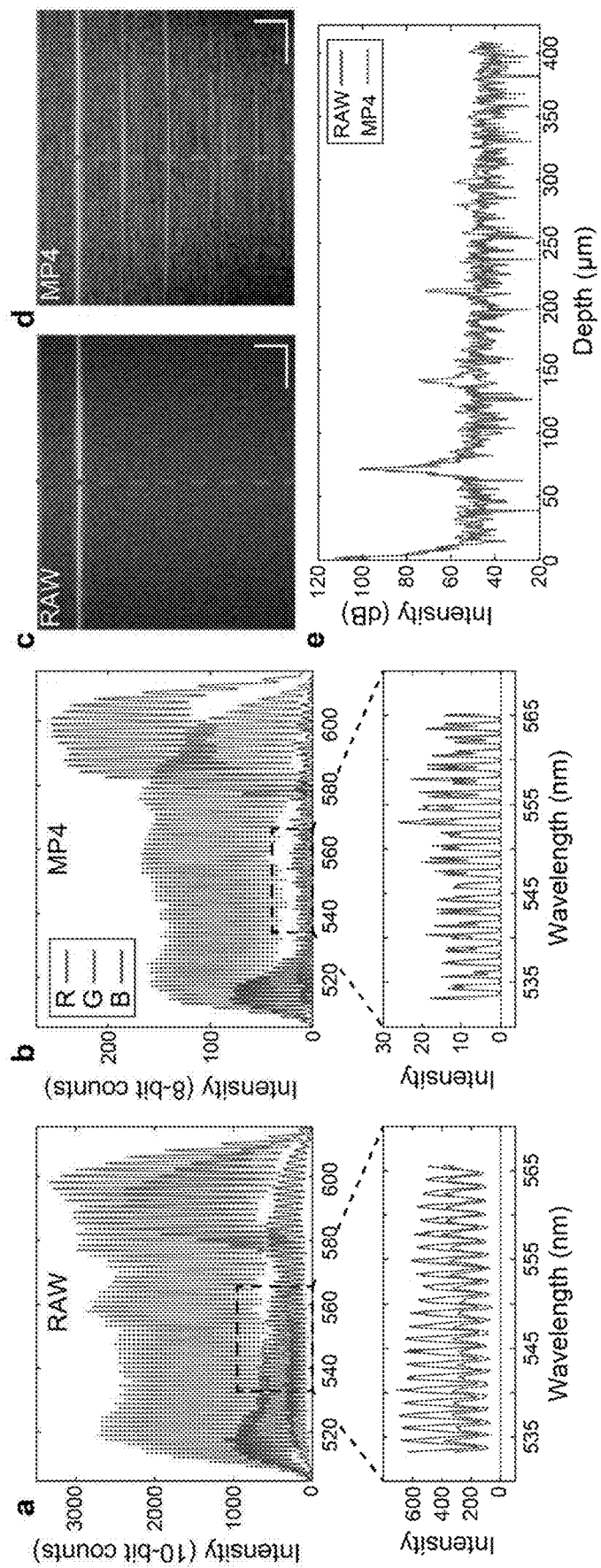
FIG. 9 illustrates plots obtained from the central row of RGB channel data of the RAW and MP4 interferograms (a) and (b), respectively. Zoom-in regions of the blue and red channels in the dotted black box of each data type showing cropping of the MP4 data at zero intensity due to the smartphone's internal processing, leading to artifacts. OCT B-scans of the mirror sample (c-d) from the full RAW data and mp4 data. A-scan from the central line of the RAW and mp4 B-scans (magenta and blue dotted lines, respectively) showing the presence of artifacts through the full depth of the A-scan. Scale bars are 100 µm along the positional axis (horizontal) and 25 µm along the depth axis (vertical).

To determine the difference in mp4 and RAW data processing by the system 100, 2D interferograms of a mirror sample were collected and saved as RAW (10-bit) and mp4 (8-bit) data types and then evaluated. Each image was acquired at an exposure time of 1/8,000 sec., an ISO of 50 and a 1× magnification. The smartphone's autofocus feature was disabled and set to a consistent value for all acquisitions. FIG. 9 (at a and b) show the RGB components from a row at the center of the FOV of the OCT interferogram for the two data types, respectively, with the black dotted box showing a zoom-in of the blue and red channels.

The zoomed in regions show a significant difference in spectral shape and intensity values between the two data types. Importantly, the mp4 spectra contain zero-valued data points where the interferogram was effectively cut off after the smartphone's internal processing. This occurred because the internal processing imparts a non-linear color scaling that is meant to make colors more aesthetically pleasing to the human eye. For scientific data, however, this scaling can lead to incorrect image content or misinterpretation of data. When processed as OCT data, the zeroed regions of the spectrum result in artifacts akin to saturation artifacts commonly seen in OCT data. To highlight these effects, FIG. 9 (at c and d) show processed B-scans of the mirror sample from the RAW and mp4 data, respectively. The RAW B-scan shows a typical OCT signal from a mirror peak, including a single sharp peak and standard speckle background, while the mp4 data contains significant artifacts throughout the full depth of the B-scan. FIG. 9 (at e) shows a comparative A-scan plot taken from the orange and blue dotted lines of the RAW and mp4 B-scans, respectively. In the experiments, the artifacts visible in the mp4 B-scan were more pronounced in highly reflective samples, but present in most test cases, including scattering samples.

Evaluating Performance and Image Capability of the System 100

The performance of the system 100 was characterized by measuring its sensitivity, SNR falloff, and lateral and axial resolutions. The system sensitivity was measured by illuminating a mirror placed in the sample arm with 10 mW of power spread laterally across 1000 pixels. The sample illumination was then attenuated using an OD-2 absorptive neutral density filter. Considering the gaussian intensity profile created by the cylindrical lens, the peak intensity was estimated to be 40 µW at the central field point. Using an exposure time of 1.25 ms, the theoretical SNR limit was 93 dB, and the obtained peak sensitivity was 84 dB.

Figure 10:
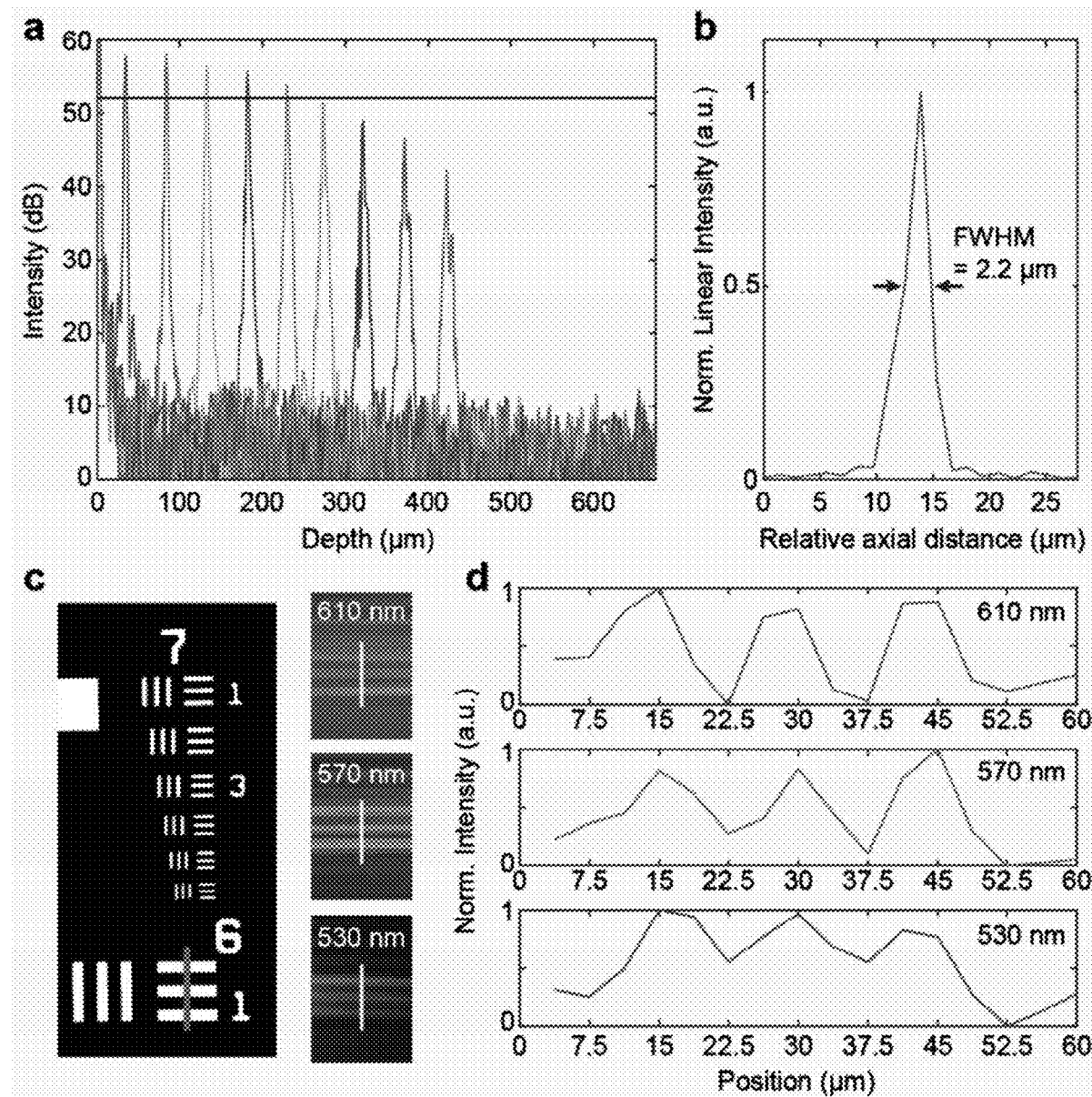
FIG. 10 illustrates the performance characterization of the smartphone-integrated OCT system of FIG. 1. (a) SNR falloff, (b) axial resolution (c) USAF chart group 7 and group 6 element 1 zoom-in and (d) lateral resolution intensity plot showing that group 6 element 1 across 3 wavelengths.

Next, the sensitivity falloff was evaluated by translating the reference mirror over a depth of 500 µm in 50-µm increments. The measured 6-dB falloff point was ~260 m, as shown in FIG. 10 (at a). The axial resolution was measured to be 2.2 µm using a mirror peak at a depth of roughly 100 µm (FIG. 10 (at b)). The 6-dB falloff point and axial resolution are worse than their theoretical values of 843 µm and 1.43 µm. This may be due to aberrations induced by the smartphone optics, specifically chromatic aberration, that can significantly reduce the achievable spectral resolution. Moreover, chromatic aberration was demonstrated as a source of axial blurring in other visible-light OCT systems.

Finally, the lateral resolution was measured by imaging a USAF-1951 chrome negative resolution chart (e.g., 38-256, available from Edmund Optics). FIG. 10 (at c) shows a representative image of group 7 and group 6 element 1 of the resolution chart and spectral images taken from three wavelengths (530 nm, 570 nm and 610 nm). FIG. 10 (at d) shows that the features of group 6 element 1, which corresponds to a resolution of 15.8 m, were clearly resolvable at each wavelength. The measured resolution was greater than the theoretical diffraction-limited spot of 6 m; this was attributed to the degradation to unknown aberrations on the transmitted spectrum associated with imaging through the reverse lens and native smartphone camera system.

Figure 11:
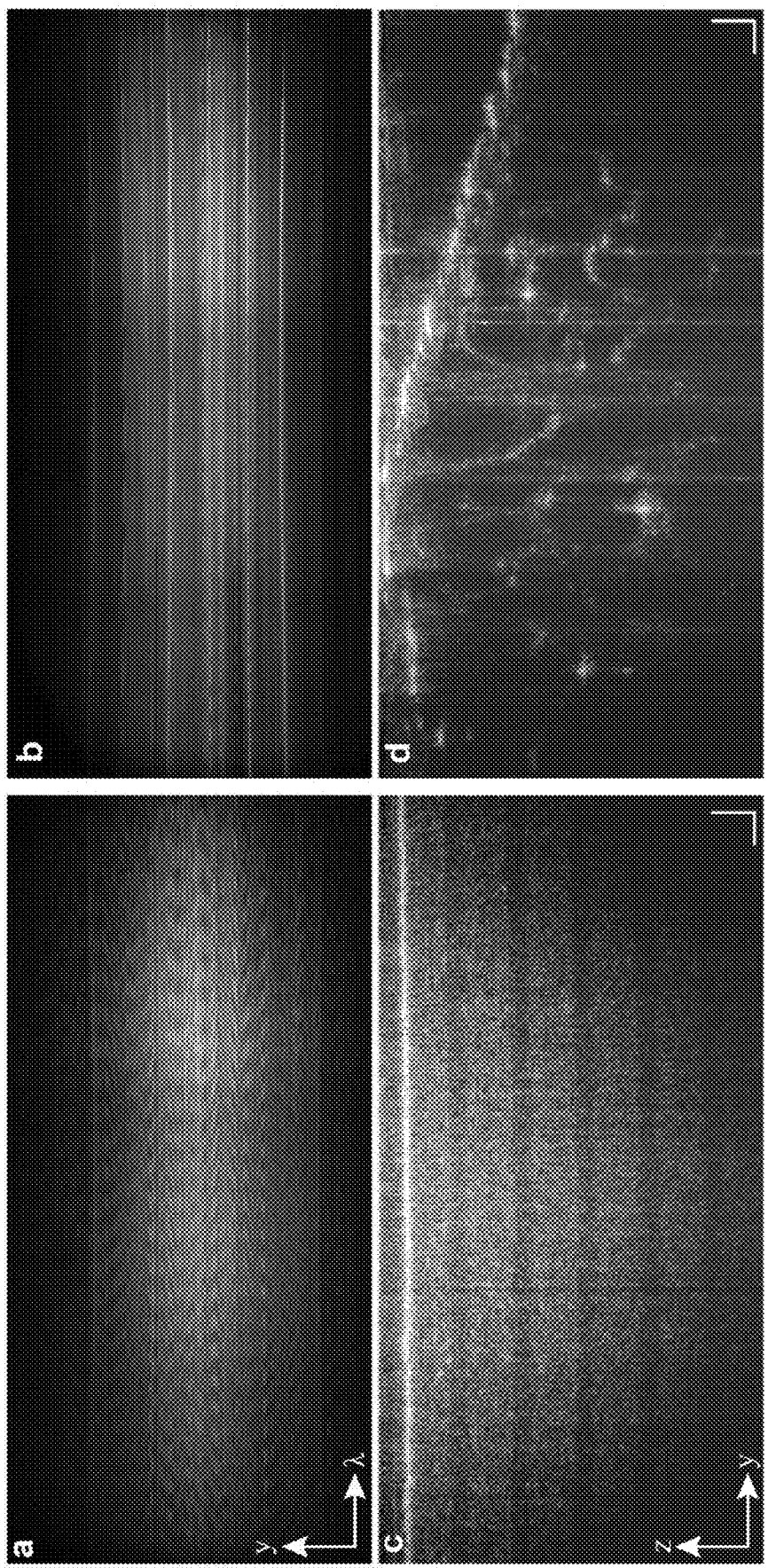
FIG. 11 illustrates sample imaging with the smartphone-integrated OCT system of FIG. 1. (a) and (b) raw spectral interferograms of tape and cucumber and the corresponding B-scans in (c) and (d), respectively. Scale bars are 150 µm along the y-axis (horizontal) and 50 µm along the z-axis (vertical).

To demonstrate the imaging capability of the system 100, two scattering samples were imaged: Scotch tape and cucumber (FIG. 11). The data were acquired using 16 mW of extended illumination on the sample and a 5-ms exposure time. FIG. 11 (at a and b) show representative single-frame raw spectra from a roll of tape and cucumber and FIG. 11 (at c and d) show 10 and 20 frame-averaged B-scans of the same samples, respectively. The image of tape shows six layers with clear differentiation of layers over a depth of ~300 μm. The image of the cucumber reveals clear cell structures. The full lateral FOV is 4 mm; however, there was notable signal reduction towards the edge of the FOV that results from the Gaussian illumination profile of the cylindrical lens and vignetting on the reverse phone lens relay.

As disclosed, the first OCT system to integrate the native smartphone optics along with custom software to visualize and acquire OCT B-scans in real time was developed. In doing so, there is potential utility of smartphones to replace some of the costly components (e.g., camera, scanner, computer, display) for OCT. In addition, an image processing pipeline was developed that improves imaging performance through native smartphone optics and enables high-performance scientific imaging that may be tailored for OCT or other imaging science applications. The importance of using RAW data rather than mp4 data was demonstrated to yield accurate images of high quality. The system 100 provides several advantages compared to traditional OCT systems. Mainly, the use of a smartphone integrates several components (camera, PC, display) that are normally separate components or devices into a single compact device.

Various features and advantages of the invention are set forth in the following claims.

What is claimed is:

1. A smartphone-integrated optical coherence tomography system comprising:
   an optical coherence tomography (OCT) system including
      a dispersion element positioned upstream of the smartphone, the dispersion element configured to receive relayed light from the sample and spectrally disperse the relayed light to generate a dispersed beam, and
      a lens group positioned to receive and focus the dispersed beam to generate a spectrum;
   a smartphone configured to receive a light signal from the OCT system, the light signal generated by reflection from a sample, the smartphone configured to generate OCT B-scans in real-time of the sample based on the light signal; and
   a reverse-lens optically coupled to the OCT system and configured to receive the spectrum from the lens group and deliver the light signal to the smartphone;
   wherein the smartphone generates RAW video data based on the spectrum of the sample, and
   wherein the smartphone includes an application stored as non-transitory computer-readable medium, the application configured to
      receive the RAW video data of the sample,
      process the RAW video data for intensity correction and distortion correction, and
      display, on the smartphone, a processed OCT B-scan of the sample.

2. The system of claim 1, wherein the smartphone is configured to display OCT B-scans in real-time of the sample based on the RAW video data of the sample.

3. The system of claim 1, wherein the application is configured to
   display, on the smartphone, the spectrum of the sample.

4. The system of claim 1, wherein the application is configured to
   display, on the smartphone, a processed OCT B-scan of the sample.

5. The system of claim 1, wherein the application is further configured to
   convert the RAW video data of the sample into an RGB-mosaicked image stack,
   scale an intensity of each RGB pixel in the RGB-mosaicked image stack to compensate for a filter in the camera in the smartphone to generate intensity-corrected data,
   apply a correction algorithm for distortions in the intensity-corrected data to generate a corrected spectral image, and
   process the corrected spectral image to generate the OCT B-scan of the sample.

6. The system of claim 1, further comprising a support platform to align the smartphone relative to the reverse-lens to receive the light signal from the OCT system.

7. The system of claim 1, further comprising a magnification relay optically coupled to the optical coherence tomography system and configured to receive the spectrum and transmit the 2D spectrum to a camera in the smartphone.

8. A smartphone-integrated optical coherence tomography system comprising:
   an optical coherence tomography (OCT) system;
   a reverse-lens configuration optically coupled to the OCT system;
   a smartphone configured to receive a light signal from the reverse-lens configuration, the light signal generated by reflection from a tissue sample, the smartphone configured to
      generate OCT B-scans in real-time of the tissue sample based on the light signal,
      generates RAW video data based on the 2D spectrum of the tissue sample,
   wherein the smartphone includes a first application stored as non-transitory computer-readable medium, the first application configured to
      display, on the smartphone, the spectrum of the tissue sample, and
      display, on the smartphone, a processed OCT B-scan of the tissue sample, and
   wherein the smartphone includes a second application stored as non-transitory computer-readable medium, the second application configured to
      receive the RAW video data of the tissue sample,
      process the RAW video data for intensity correction and distortion correction, and
      display, on the smartphone, a processed OCT B-scan of the tissue sample.

9. The system of claim 8, wherein the reverse-lens configuration includes a magnification relay optically coupled to the OCT system.

* * * * *